United States Patent [19]
Gould et al.

[11] Patent Number: 5,215,701
[45] Date of Patent: Jun. 1, 1993

[54] PROCESS FOR MAKING A SURGICAL GLOVE

[75] Inventors: Arnold S. Gould, 3 Clark Rd., Bedford, Mass. 01730; Raymond P. Fedors, Foxboro, Mass.

[73] Assignee: Arnold S. Gould, Bedford, Mass.

[21] Appl. No.: 890,371

[22] Filed: May 26, 1992

Related U.S. Application Data

[60] Continuation of Ser. No. 657,437, Feb. 19, 1991, abandoned, which is a division of Ser. No. 430,624, Nov. 1, 1989, Pat. No. 5,001,354, which is a continuation of Ser. No. 85,962, Aug. 14, 1987, abandoned.

[51] Int. Cl.$^5$ .................. B28B 1/38; B29C 41/14
[52] U.S. Cl. ................ 264/331.13; 264/255; 264/299; 264/301
[58] Field of Search ............ 264/215, 216, 255, 299, 264/303, 305, 306, 307, 308, 330, 331.13, 301

[56] References Cited

U.S. PATENT DOCUMENTS

| | | | |
|---|---|---|---|
| 2,482,418 | 9/1949 | Jenkins | 264/215 |
| 3,185,751 | 5/1965 | Sutton | 264/305 |
| 3,536,920 | 10/1970 | Sedlak | 250/108 |
| 3,864,124 | 2/1975 | Breton et al. | 264/127 |
| 3,883,749 | 5/1975 | Whittaker et al. | 250/516 |
| 4,194,040 | 3/1980 | Breton et al. | 264/127 |
| 4,957,884 | 9/1990 | Knudsen et al. | 264/127 |
| 5,001,354 | 3/1991 | Gould et al. | 250/516.1 |

Primary Examiner—Jan H. Silbaugh
Assistant Examiner—A. Y. Ortiz
Attorney, Agent, or Firm—Pandiscio & Pandiscio

[57] ABSTRACT

Pinhole-free, radiation absorbing, surgical quality latex gloves are formed from homogeneous suspension of natural rubber and high specific gravity metal or metal compound. The suspension is formed under conditions which prevent entrapment of gas in the suspension.

12 Claims, 1 Drawing Sheet

PROCESS FOR MAKING A SURGICAL GLOVE

This is a continuation of copending application Ser. No. 07/657,437 filed on Feb. 19, 1991, now abandoned, which is a division of Ser. No. 07/430,624 filed on Nov. 1, 1989, now U.S. Pat. No. 5,001,354, which is a continuation of Ser. No. 07/085,962 filed on Aug. 14, 1987, now abandoned.

BACKGROUND OF THE INVENTION

At the present time, procedures in various medical areas such as radiology and orthopedics, require physicians to place their hands near or even in a fluoroscopic field. These procedures are relatively new and provide improved patient care, less traumatic operations and shortened recovery periods Such procedures include percutaneous kidney stone removal or percutaneous biliary shunt placement, both of which has virtually replaced open surgical procedures and are performed by radiologists. In orthopedics, blind nailing of bones such as the femur are also much less invasive and are increasingly replacing open surgical procedures In all of these procedures, however, the physician is required to work for prolonged periods of time under fluoroscopic guidance with the physician's hands near or in the fluoroscopic field. An active physician performing these type of procedures will rapidly accumulate high doses of ionizing radiation to the hands, often well above the limits allowed The International Council for Radiation Protection currently recommends a dose limit of not more than 50 rems/year to the hands. During certain non-vascular procedures, exposure to the hands has been shown to be about 33 times more than the dose received at the physician's face.

Thus, there is a present need for providing a surgical glove having good tactile sense in order to permit the physician to perform the procedures involved and that the glove provide fully effective hand protection to the physician against exposure to X-rays. That is, the glove must have an X-ray absorbing composition uniformly distributed throughout the glove and be free of pin holes. Presently, there are available lead oxide loaded gloves produced from polyurethane or polyvinylchloride. Unfortunately, these gloves lack the tactile sense needed for surgical use since they are essentially non-stretchable due to the nature of polyurethane or other material compared with natural latex rubber, and this is exacerbated by the heavy loading with lead oxide. Examples of such gloves are disclosed in U.S. Pat. Nos. 3,025,403; 3,045,121; 3,185,751 and 3,883,749. None of these patents discloses a means for preparing gloves from natural latex which are free of pinholes. In addition, the prior art gloves are relatively ineffectual for attenuating X-rays. For example, in the ranges normally used, e.g., 80-100 kilovolts, these gloves absorb only about 20% of the incident radiation. These gloves also share the common drawback in that their production is dangerous since lead oxide is toxic. Accordingly, it would be highly desirable to provide a glove having a tactile sense which permits their use in surgery as well as a glove capable of attenuating substantially greater amounts of incident radiation as compared to presently available gloves. It would be highly desirable to provide an X-ray absorbing glove from natural latex since gloves produced from latex are highly stretchable. However, there is no presently available process for producing high particle density loaded latex gloves which avoids latex coagulation and/or air entrapment while maintaining a homogeneous latex mix. Thus, there is no presently available method for making thin loaded latex gloves free of pin holes.

SUMMARY OF THE INVENTION

The present invention provides surgical gloves containing particles having a high specific gravity at a concentration which permits the gloves to absorb a high percentage of incident radiation. The particles can comprise a metal or a metal compound which has a specific gravity of at least 11. The metal or metal compound particles are admixed with a natural rubber latex composition under conditions which avoid latex coagulation and which avoid cavitation or any entrainment of air at all at the exposed top surface of the mixture in a container until a substantially uniform mixture of the resulting composition is produced. The glove is produced from the latex metal or metal compound mixture by dipping a glove form into the mixture and allowing the mixture to dry on the form. The glove can be formed from one or a multiplicity of layers which multiplicity of layers can include a natural rubber latex layer of filler particles.

DESCRIPTION OF SPECIFIC EMBODIMENTS

In accordance with the present invention, it has been found that particles having a high specific gravity can be maintained substantially uniformly in suspension in a natural rubber latex free of air bubbles in order to afford the production of radiation resistant surgical gloves therefrom free of pin holes. The gloves are formed from one or a multiplicity of layers comprising dried natural rubber latex wherein at least one of the layers includes high specific gravity particles uniformly distributed therethrough. As used herein the term "high specific gravity particles" refers to metal or metal compound particles having a specific gravity of at least 11.0. Representative suitable high specific gravity particles include tungsten, tantalum, tungsten carbide, tungsten oxide, or mixtures thereof. The high specific gravity particles have an average size of less than about 5 microns and preferably less than about 1 micron.

Figure 1:
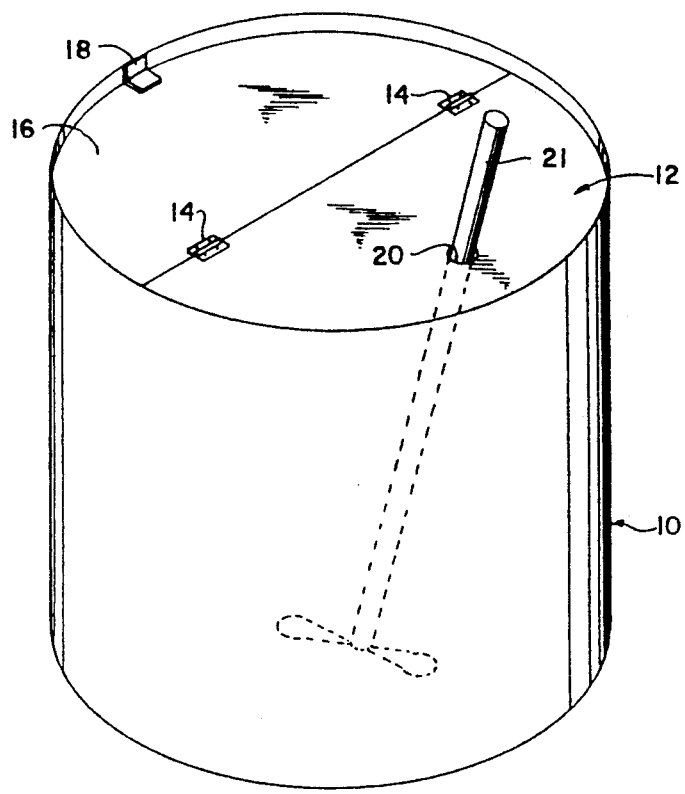
FIG. 1 is a perspective view of a mixing container which can be utilized in the present invention.

A suspension of the high specific gravity particles in the natural rubber latex is produced by agitating a mixture of the particles and the latex under conditions to prevent the particles from precipitating to the bottom of the mixture while avoiding entrapment of air within the latex-particle mixture. Referring to FIG. 1, in one embodiment of the present invention, the natural rubber latex and high specific gravity particles are added to a container 10 having a top 12 which floats on top of the latex-particle mixture The top 12 has hinges 14 so that top section 16 can be opened by means of handle 18 in order to permit dipping of a glove form (not shown) into the latex-particle suspension immediately after ceasing agitation thereby to prevent air entrapment. After dipping, the hinged top section 16 is closed and agitation is resumed The top 12 is provided with a hole 20 through which an agitator 21 can be extended to effect the agitation of the suspension. A suitable agitator can comprise a rod having attached at one end a propellor which is located at or near the bottom of the container 10. The rate of agitation of the agitator is controlled so that cavitation of the top surface of the suspension is not effected by causing the top 12 to float on top of the suspension, the possibility of cavitation of the suspension at the top surface is vastly reduced or eliminated. Thus, in this manner, the particles can be retained in suspension substantially uniformly within the natural rubber latex while avoiding entrapment of air within the suspension. Entrapment of air within the suspension is to be avoided since rubber gloves produced therefrom will have pin holes or larger holes upon curing due to the presence of air.

Figure 2:
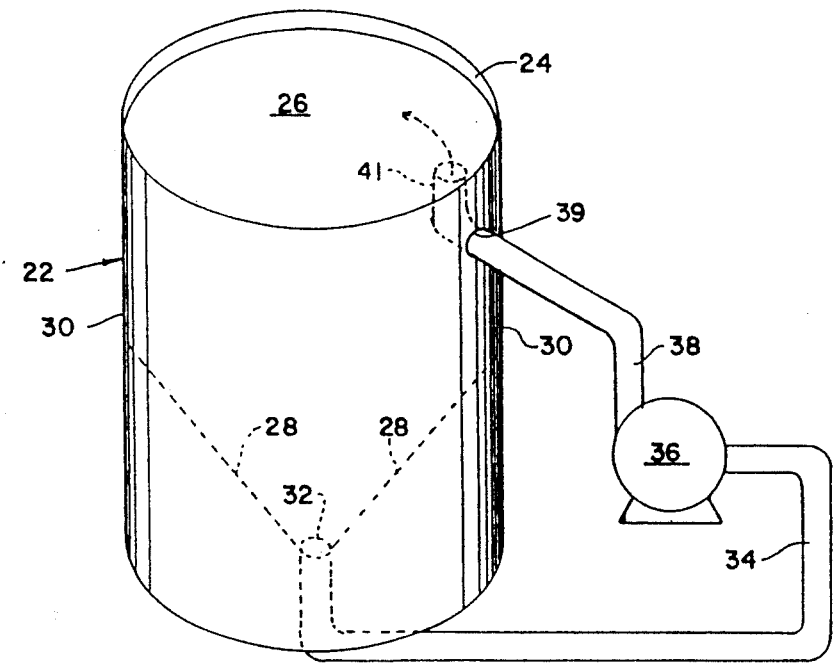
FIG. 2 is a perspective view of an alternative mixing means which can be utilized in the present invention.

Referring to FIG. 2, an alternative embodiment is shown for effecting agitation of the suspension while avoiding entrapment of air A container 22 is provided having an open top 24 so that the top surface 26 of the latex-particle suspension is exposed to the atmosphere. The container 22 has a conical shaped bottom having walls 28 positioned at an angle to the vertical axis of the container between about 15° and about 45°, preferably between about 30° and about 20°. The walls 28 extend to a bottom opening 32 which is connected to a conduit 34 and a low shear pump 36. The suspension is recirculated through a conduit 38 to a point between about $\frac{1}{2}$ and about 2 inches below the top surface 26. A screen or filter 39 optionally can be positioned at the end of conduit 38. The pump 36 is a low shear pump which prevents coalescence of the latex caused by shearing forces on the latex. Representative suitable low shear pumps are peristaltic pumps, diaphragm pumps or double diaphragm pumps. The pump rate is high-er than the free fall particle rate in the latex. This free fall particle rate can be easily determined by measuring the drop rate of the particles in the latex in a separate container prior to forming the desired suspension. However, the pump rate must not be so high as to entrap air bubbles in the suspension. The actual pump rate will vary depending upon the type of natural rubber latex utilized, the specific particles utilized and the sixe of the container. Generally, the pump rates will vary between about 0.5 gallons per minute and 3 gallons per minute, for one-form dipping vats, usually between about 0.7 and 1.5 gallons per minute. The latex particle suspension is reintroduced into container 22 from conduit 38 in a direction essentially parallel to the plane of the top surface of the suspension in container 22. In addition, the suspension is introduced into container 22 at an angle relative to the inner surface or container 22 so that direct impingement on the inner surface is avoided. That is, the angle relative to the inner surface at which the suspension is initially introduced from conduit 38 and nozzle 41 should be as parallel to the inner surface as possible When using either embodiment shown in FIG. 1 or in FIG. 2, make up suspension is periodically added to the container in order to prevent entrapment of air during mixing.

The latex-particle suspension is formed from natural rubber particles in a liquid suspending medium, typically water. The high specific gravity particles comprise between about 3 and about 20 volume percent, preferably between 5 and 10 volume percent based upon the volume of the latex-particle suspension. The latex also can include conventional dispersing agents such as sulphonated naphthalene or stabilizing agents such as polyethylene oxide condensation products.

When forming gloves, a conventional glove form having the general shape of a human hand is dipped into the latex-suspension which is then allowed to dry on the form thereby to form a continuous glove layer on the glove form. The latex may be utilized in conjunction with a conventional latex coagulant such as calcium nitrate in a mixture of water and ethanol.

The glove can be formed by any one of a plurality of dipping steps In one procedure, a glove form is first dipped into pure natural rubber latex without filler, removed therefrom and dried to a hazy appearance. Thereafter, the glove form is dipped into the latex-high specific gravity particle suspension, removed therefrom and dried as set forth above. Lastly, the glove form is dipped into the pure natural rubber latex free of filler, and then is oven-cured at about 170° F. to 210° F. for about 30 to 60 minutes.

In a second procedure, the glove form is dipped into the coagulant solution, dried for about 2 to 5 minutes and then dipped into the latex-high specific gravity particle suspension and dried for about 2 to 5 minutes. Thereafter, the glove is leached in hot water for about 30–60 minutes to wash away excess coagulant and then is oven-cured at about 170° F. to 210° F. for about 30 to 60 minutes.

It is preferred that the coagulant utilized herein include water as the solvent. It has been found that water generally evaporates at a slower rate than hydrocarbon suspending agent normally employed When the gloves are dried with the fingers and thumb up and water is utilized as the suspending agent, there is some migration of coagulant away from the tips of the finger and thumb on the glove form which results in these areas being thinner than the remaining areas of the glove. This further results in improved tactile sense for the user in the working areas of the hand while at the same time providing the desired protection against radiation.

The gloves of this invention generally have a thickness of between about 6 and about 20 thousandths of an inch, preferably between about 10 and about 15 thousandths of an inch. These gloves provide improved protection and retain the tactile sense necessary in surgical procedures The gloves of this invention are capable of absorbing generally between about 50 and about 80 percent of incident radiation as compared with the currently available lead oxide-polyurethane glove which absorbs only between about 10 and about 30 percent of incident radiation of between about 60 to 100 KVP.

The following examples illustrate the present invention and are not intended to limit the same.

EXAMPLE 1

Using the apparatus as shown in FIG. 1, a double impeller two inch blade was utilized at 1200 rpm. The blade was positioned immediately adjacent the bottom inner surface of the container. Tungsten particles (17.5 lb.) having an average particle size of 0.8 microns were mixed in a container with 1850 ml water containing 0.9 wt percent sulfonated naphthalene, Rohm and Haas (Tamol 731) based on solids for about 30 minutes in order to coat the particles with the Tamol dispersing agent and to form a creamy, homogeneous dispersion. The dispersion was added to a natural rubber latex in the container shown in FIG. 1. The latex comprised 55 vol. % solids and the final mixture comprised 13 vol.% tungsten particles Agitation was initiated and maintained until a uniform, air-free latex-particle suspension was formed. Immediately after agitation was stopped, the container lid was opened and a glove form was dipped into the latex-particles suspension for 20–30 seconds. The forms were removed slowly to form a thin latex layer on the forms. The container lid was then closed and agitation was resumed. The form was then inverted back and forth for 5 minutes to cause the latex to gel. The form was then inserted into a coagulant comprising 30% calcium nitrate in 90 vol. % water and 10 vol % ethanol for 30 seconds. After inverting the form for 5 minutes the form was again dipped in the latexparticle suspension after agitation was stopped. The form was again removed slowly, the lid closed and agitation restarted. Thereafter the latex gloves on the forms were dipped in hot water for 45 minutes to wash out any water washable compositions in the gloves. The gloves were then oven cured for 30 minutes at 190° F. The gloves were free of pinholes and absorbed 65% of incident radiation at 60 KVP.

EXAMPLE 2

Using the apparatus shown in FIG. 2, the included angle between the conical walls 28 was 60° and the hole 32 had a ¾ inch diameter. A peristaltic pump was used at a recirculation rate of 0.9 gallons per minute. The tube 38 had an inside diameter of ½ inch. The nozzle 41 had a 45° elbow and was positioned to flow effluent therefrom substantially parallel to the plane of the top surface of the latex suspension in the container 22. Tungsten particles having an average particle size of 0.8 microns were mixed in a container with 0.2% Rohm and Haas sulfonated naphthalene (Tamol 731) in distilled water for about 60 minutes in order to coat the particles with dispersing agent. The homogenous dispersion created was added to a natural rubber latex in the container shown in FIG. 2. The latex comprised 60 vol. % solids and the final mixture comprised 10 vol. % tungsten particles. Pumping was initiated and maintained until a uniform, airfree latex-particle suspension was formed. A glove form was dipped into a 27% aqueous solution of calcium nitrate and then dried inverted for 10 minutes. While pumping, a glove form was dipped into the latex-particle suspension for 20 seconds. The form was removed slowly to form a thin latex layer on the form. The form was then inverted back and forth for 5 minutes to cause the latex to gel. Thereafter the latex glove on the form was dipped in hot water for 45 minutes to wash out water washable compositions in the glove. The glove was then oven cured for 30 minutes at 190° F. The glove was free of pinholes and absorbed 70% of incident radiation at 70 KVP.

We claim:

1. The process for forming a radiation-absorbing glove having a wall thickness between about 6 and 20 thousands of an inch which comprises the steps of:
   forming a mixture comprising high specific gravity metal or metal compound particles and a latex composition, said latex composition including rubber particles suspended in a liquid carrier, said metal or metal compound particles comprising between about 5 and 10 volume percent of said mixture, and said mixture having a consistency such that said metal or metal compound particles will readily settle out of said mixture and entrapped air will readily bubble out of said mixture;
   agitating said mixture so as to disperse said metal or metal compound particles substantially uniformly throughout said latex composition without the entrapment of air in said mixture;
   depositing said agitated mixture onto a glove form;
   coagulating said deposited mixture on said glove form; and
   curing said coagulated mixture on said glove form to form a glove;
   said glove being formed so as to comprise at least one layer comprising a mixture of cured rubber latex and high specific gravity metal or metal compound particles, said at least one layer being pin-hole free and being capable of absorbing between about 50 and 80 percent of incident radiation of between about 60 to 100 KVP, and said glove being sufficiently flexible to permit it to be used with dexterity during a medical procedure.

2. The process of claim 1 wherein said mixture is formed in a container and has a top surface, and wherein substantially the entire top surface of said mixture is sealed from the atmosphere during said agitating step.

3. The process of claim 1 wherein said mixture is formed in a container and has a top surface, said container having a bottom defining an opening, and wherein said agitating step comprises utilizing low shear pumping means to circulate said mixture from said opening to a point near to, but below, said top surface of said mixture, the rate of circulation being sufficient to maintain said high specific gravity metal or metal compound particles in substantially uniform suspension within said latex composition and being lower than the rate at which air is entrained by said top surface.

4. The process according to claim 1 wherein said high specific gravity metal or metal compound particles comprise tungsten particles.

5. The process according to claim 2 wherein said high specific gravity metal or metal compound particles comprise tungsten particles.

6. The process according to claim 3 wherein said high specific gravity metal or metal compound particles comprises tungsten particles.

7. The process for forming a radiation-absorbing glove having a wall thickness between about 6 and 20 thousands of an inch which comprises the steps of:
   forming a mixture comprising high specific gravity metal or metal compound particles and a latex composition, said latex composition including rubber particles suspended in a liquid carrier, said rubber particles comprising between about 55 and 60 volume percent of said latex composition, and said metal or metal compound particles comprising between about 5 and 10 volume percent of said mixture;
   agitating said mixture so as to disperse said metal or metal compound particles substantially uniformly throughout said latex composition without the entrapment of air in said mixture;
   depositing said agitated mixture onto a glove form;
   coagulating said deposited mixture on said glove form; and
   curing said coagulated mixture on said glove form to form a glove;
   said glove being formed so as to comprise at least one layer comprising a mixture of cured rubber latex and high specific gravity metal or metal compound particles, said at least one layer being pin-hole free and being capable of absorbing between about 50 and 80 percent of incident radiation of between about 60 to 100 KVP, and said glove being sufficiently flexible to permit it to be used with dexterity during a medical procedure.

8. The process of claim 7 wherein said mixture is formed in a container and has a top surface, and wherein substantially the entire top surface of said mixture is sealed from the atmosphere during said agitating step.

9. The process of claim 7 wherein said mixture is formed in a container and has a top surface, said container having a bottom defining an opening, and wherein said agitating step comprises utilizing low shear pumping means to circulate said mixture from said opening to a point near to, but below, said top surface of said mixture, the rate of circulation being sufficient to maintain said high specific gravity metal or metal compound particles in substantially uniform suspension within said latex composition and being lower than the rate at which air is entrained by said top surface.

10. The process according to claim 7 wherein said high specific gravity metal or metal compound particles comprise tungsten particles.

11. The process according to claim 8 wherein said high specific gravity metal or metal compound particles comprise tungsten particles.

12. The process according to claim 9 wherein said high specific gravity metal or metal compound particles comprise tungsten particles.

* * * * *